(12) United States Patent
Tappeiner

(10) Patent No.: US 6,928,663 B1
(45) Date of Patent: Aug. 16, 2005

(54) GOGGLE CLIP

(75) Inventor: Marc Tappeiner, Goleta, CA (US)

(73) Assignee: Bushnell Performance Optics, Overland Park, KS (US)

( * ) Notice: Subject to any disclaimer, the term of this patent is extended or adjusted under 35 U.S.C. 154(b) by 10 days.

(21) Appl. No.: 10/835,645

(22) Filed: Apr. 30, 2004

(51) Int. Cl.[7] .................................................. A61F 9/02

(52) U.S. Cl. ....................................................... 2/436

(58) Field of Search ........................ 2/436, 451, 453, 2/426

(56) References Cited

U.S. PATENT DOCUMENTS 6,047,410 A * 4/2000 Dondero ........................ 2/426
6,131,246 A * 10/2000 Paulson et al. ......... 24/265 BC

OTHER PUBLICATIONS www.spyoptic.com.
www.smithsport.com.

* cited by examiner

Primary Examiner—John Calvert
Assistant Examiner—Brian Kauffman
(74) Attorney, Agent, or Firm—Hovey Williams LLP

(57) ABSTRACT

A goggle clip (10) that may be used to rotatably or pivotally secure a strap (12) to a goggle (14) with a concealed hinge. The clip (10) broadly comprises a main body (24) located outside a shroud (20) of the goggle (14) and secured to the strap (12), an axle (26) located inside the shroud (20), and a forwardly extending skirt (30) that substantially conforms to the shroud (20). The skirt (30) preferably maintains close proximity to the shroud (20) during rotation of the clip (10). Thus, the skirt (30) forms an aerodynamic seal with the shroud (20), thereby diverting airflow away from the hinge and preventing wind, dust, dirt, and other contaminants from interfering with the hinge's operation. Furthermore, the skirt (30) and the location of the axle (26) conceal the hinge, thereby providing a more aesthetically appealing goggle (14).

9 Claims, 2 Drawing Sheets

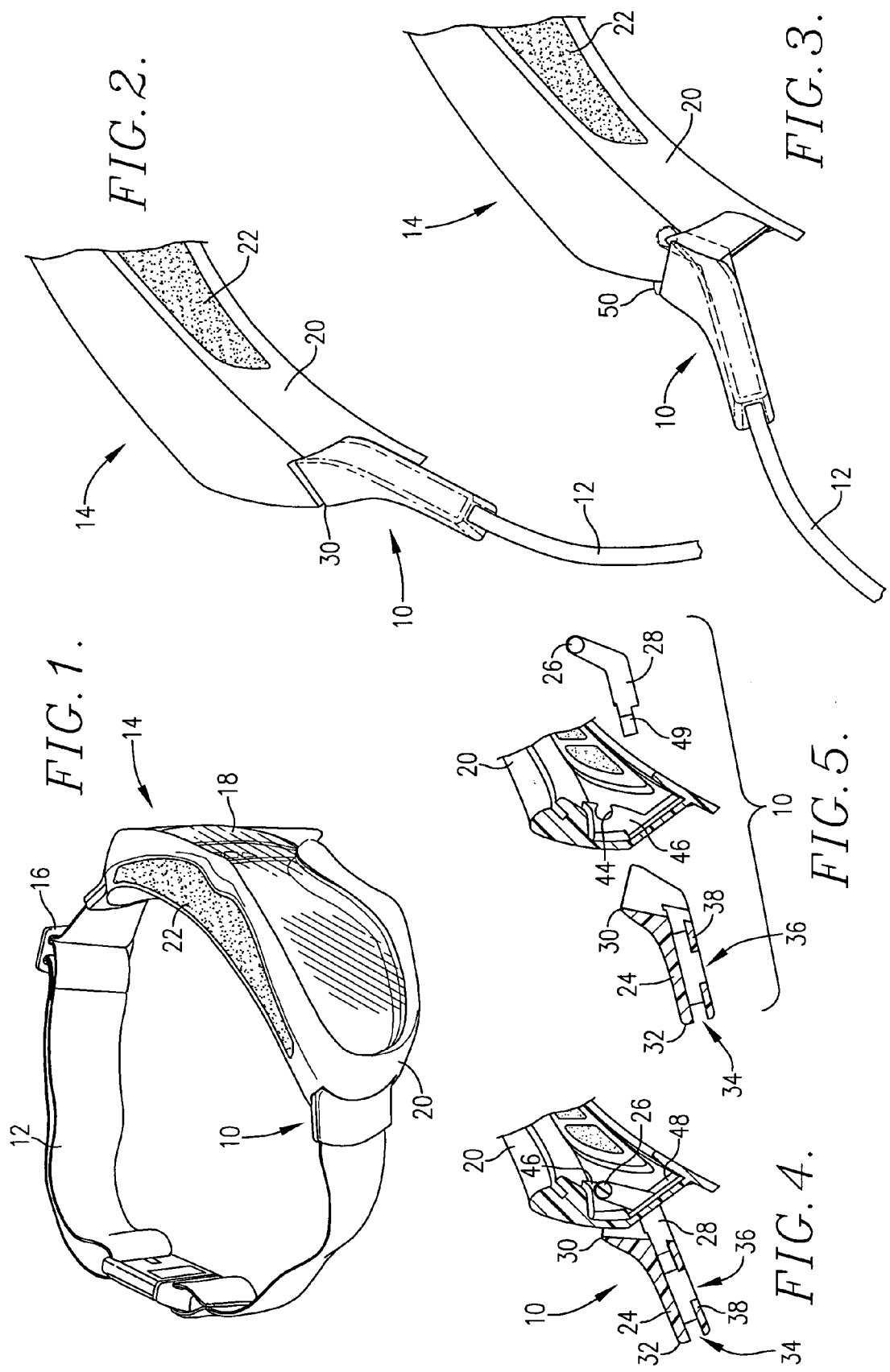

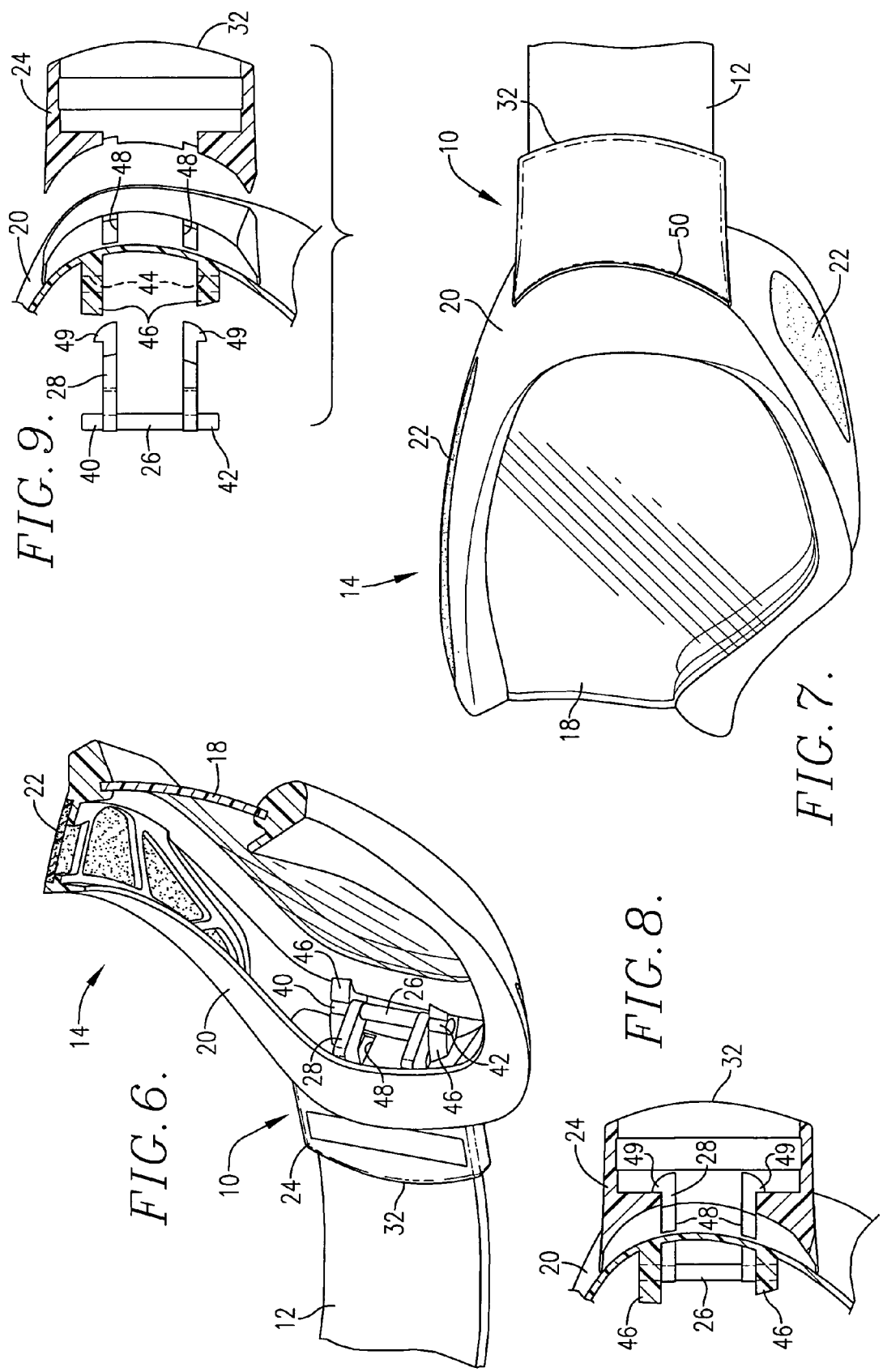

GOGGLE CLIP

BACKGROUND OF THE INVENTION

1. Field of the Invention

The present invention relates to goggles. More particularly, the invention relates to a goggle clip that may be used to rotatably or pivotally secure a strap to a goggle with a concealed hinge.

2. Description of Prior Art

Skiers and snow-boarders, as well as other outdoors enthusiasts, often wear goggles to protect their eyes from the sun, wind, snow, and contaminants. Occasionally, skiers and snow-boarders also desire to wear helmets to protect their heads from potential impacts. Conventional goggles don't fit well over helmets because the helmets interfere with the goggle's straps where the straps meet the goggle body. Specifically, the helmet's thickness forces the goggle's strap outward and away from a user's face, thereby preventing the goggle from sealing to the user's face.

To alleviate this problem, goggles with outward extensions, which offset the strap from the goggle body, have been designed to reduce the interference between helmets and goggle straps. Unfortunately, however, the extensions of these goggles are unattractive when not worn with a helmet. Furthermore, the extensions interfere with proper fit and comfort when such goggles are not worn with a helmet. Therefore, skiers and snow-boarders have been forced to choose between a goggle designed to be used with a helmet and a goggle designed to be used without a helmet.

In response, goggles with hinge mechanisms which allowed goggles to be used either with or without a helmet were developed. These hinge mechanisms may fold outwardly, thereby offsetting the strap from the goggle body, for use with a helmet. These hinge mechanisms may also fold inwardly, thereby positioning the strap adjacent the goggle body, for use without a helmet. However, such hinge mechanisms are unsightly and may become clogged with snow or dirt, thereby inhibiting their functionality.

Accordingly, there is a need for an improved goggle clip that overcomes the limitations of the prior art.

SUMMARY OF THE INVENTION

The present invention overcomes the above-identified problems and provides a distinct advance in the art of goggles. More particularly, the present invention provides a goggle clip that may be used to rotatably or pivotally secure a strap to a goggle with a concealed hinge. The strap and goggle are preferably substantially conventional. For example, the goggle preferably comprises a rigid lens for protecting the user's eyes, and a shroud surrounding the lens' periphery. The shroud preferably extends rearwardly of the lens to engage the user's face, and thereby hold the lens offset forwardly of the user's face.

The clip preferably includes a main body located outside the shroud and secured to the strap, an axle located inside the shroud and offset from the main body by two support arms which penetrate the shroud, and a skirt that substantially conforms to the shroud. The main body preferably includes an arcuate distal edge having a slot therein through which the strap may be secured.

The axle is preferably secured to the shroud at a top end and a bottom end. The ends preferably fit within circular cut-outs defined by support walls within the shroud. The arms are preferably molded onto the axle, such that the axle and the arms form a unitary member, and may include outwardly extending protrusions to selectively engage the main body, thereby rigidly aligning the axle with the main body. More specifically, the arms are preferably inserted through the slots in the shroud, pushed together, inserted into the main body, and then released. The arms push outwardly on the protrusions, which engage the main body's interior, thereby securing the arms to the main body. The axle is then seated within the cut-outs, thereby rotatably or pivotally securing the clip to the goggle.

The skirt preferably extends forwardly of the main body and maintains close proximity to the shroud during rotation of the clip such that a gap between the shroud and the skirt is preferably maintained at one sixteenth of an inch or less. In this manner, the skirt forms an aerodynamic seal with the shroud, thereby diverting airflow away from the hinge and preventing snow, wind, dust, dirt, and other contaminants from interfering with the hinge's operation. Furthermore, the skirt and the location of the axle both contribute to conceal the hinge, thereby providing a more aesthetically appealing goggle.

It should be noted that the advancement of the present invention is achieved without sacrificing functionality. Specifically, the clip may still pivot freely, thereby allowing the user to selectively utilize the goggle either with our without a helmet. For example, the user may tighten the strap slightly and wear the goggle without the helmet. In this case, the clip would pivot rearwardly and inwardly-toward the user's head. The skirt would slide rearwardly along the shroud minimizing the gap. In this manner, the clip allows the strap to hold the goggle against the user's face, thereby protecting the user's eyes, while concealing the hinge.

Alternatively, the user may expand the strap slightly and wear the goggle over the helmet. In this case, the clip would pivot forwardly and away from the user's head. The skirt would slide forwardly along the shroud minimizing the gap. In this manner, the clip allows the strap to hold the goggle against the user's face, thereby protecting the user's eyes, while concealing the hinge and accommodating the helmet.

BRIEF DESCRIPTION OF THE DRAWINGS

A preferred embodiment of the present invention is described in detail below with reference to the attached drawing figures, wherein:

FIG. 1 is a perspective view of a goggle clip constructed in accordance with a preferred embodiment of the present invention and shown securing a strap to a goggle;

FIG. 2 is a plan view of the clip, strap, and goggle, showing the clip rotated rearwardly, as may be the case where the goggle is used without a helmet;

FIG. 3 is a plan view of the clip, strap, and goggle, showing the clip rotated forwardly, as may be the case where the goggle is used with a helmet;

FIG. 4 is a cut-away close up plan view of the clip;

FIG. 5 is an expanded view of FIG. 4;

FIG. 6 is another perspective view of the clip, strap, and goggle, showing an interior of a shroud of the goggle;

FIG. 7 is a side elevation view of the clip, strap, and goggle;

FIG. 8 is a cut-away close up elevation view of the clip; and

FIG. 9 is an expanded view of FIG. 8.

DETAILED DESCRIPTION OF A PREFERRED EMBODIMENT

Referring to FIGS. 1–3, the preferred goggle clip 10 constructed in accordance with a preferred embodiment of the present invention is illustrated securing a strap 12 to a goggle 14. The strap 12 is preferably substantially conventional. For example, the strap 12 is preferably flexible and resilient, in order to adequately hold the goggle 14 to a user's head. Thus, the strap 12 is preferably constructed from an elastic material approximately one and one half inches wide and approximately one sixteenth of an inch thick. The strap's 12 length is preferably designed to meet a user's needs. For example, users having relatively small heads will likely prefer the strap 12 to be shorter than users having relatively large heads. Additionally, the strap 12 preferably includes an adjustment buckle 16 to adjust the strap's 12 length such that the goggle 14 may be selectively used with and without a helmet and by a variety of users.

The goggle 14 preferably comprises a rigid lens 18 for protecting the user's eyes and a shroud 20 surrounding the lens' 18 periphery. Both the lens 18 and the shroud 20 are also preferably substantially convention, except for differences which will be made apparent below. For example, the goggle 14 is preferably substantially similar to that shown in "GOGGLE HAVING A TINTED PLASTIC LENS", U.S. Pat. No. 6,138,286, filed Apr. 14, 1999, and issued Oct. 31, 2000, hereby incorporated into the present application by reference. While the lens 18 is preferably unitary, such that the lens 18 protects both of the user's eyes, the goggle 14 may include one or more lenses 18, with each lens 18 designed to protect only one of the user's eyes.

In any case, the shroud 20 preferably extends rearwardly of the lens 18 to engage the user's face, and thereby hold the lens 18 offset forwardly of the user's face. The shroud 20 is preferably substantially flexible, and is therefore preferably constructed of rubber or another resilient material. Flexibility provides the user with a comfortable fit. Flexibility also allows the goggle 14 to conform to the user's face thereby forming a seal with the user's face. In this manner, the goggle 14 may effectively keep snow, wind, dust, dirt, and other contaminants away from the user's eyes.

The shroud 20 may include vents 22 operable to allow airflow though the goggle 14 in order to prevent fogging of the lens 18. The vents 22 may be a collection of small holes that effectively filter snow, wind, dust, dirt, and other contaminants. Alternatively, the vents 22 may be larger. In this case, the vents 22 are preferably covered by a porous material, such as open cell foam rubber, that can provide the filtering function described above while still allowing airflow through the goggle 14.

The clip 10 pivotally secures the strap 12 to the shroud of the goggle 14 and is preferably constructed from plastic or another composite material. Referring also to FIGS. 4–5, the clip 10 preferably includes a main body 24 located outside the shroud 20 and secured to the strap 12, an axle 26 located inside the shroud 20 and offset from the main body 24 by two support arms 28 which penetrate the shroud 20, and a skirt 30 that substantially conforms to the shroud 20. The main body 24 is preferably approximately one inch wide, approximately one and one half inches tall, approximately one quarter inch thick, and substantially hollow. The main body 24 preferably includes an arcuate distal edge 32 having a slot 34 therein through which the strap 12 may be secured. To further aid securement of the strap 12, the main body 24 may include a slot 36 in a rear face 38. In this manner, the strap 12 may be fed into the slot 34 in the distal edge 32 and out the slot 36 in the rear face 38 and then folded back on and secured to itself. However, the main body 24 may be secured to the strap 12 in virtually any conventional manner.

Referring also to FIGS. 6–9, the axle 26 is preferably substantially vertically aligned such that the clip 10 rotates or pivots about a vertical axis defined by the axle 26. The axle 26 is preferably secured to the shroud 20 at a top end 40 and a bottom end 42. The ends 40,42 preferably fit within circular cut-outs 44 defined by support walls 46 within the shroud 20. The walls 46 are preferably constructed of the same material as the rest of the shroud 20, thereby simplifying construction of the goggle 14. However, the walls 46 may be constructed of a different material. For example, the walls 46 may be constructed of a more rigid material, thereby more securely holding the axle 26 in place. In any case, the axle 26, the arms 28, and the walls 46 form a hinge, allowing the clip 10 to rotate or pivot with respect to the shroud 20.

The arms 28 are preferably molded onto the axle 26, such that the axle 26 and the arms 28 form a unitary member. The arms 28 are preferably arcuate, such that they form an approximately one hundred and thirty-five degree angle. However, the arms 28 may form other angles. For example, where more extreme curvature is required, the arms 28 may form a ninety degree angle, or anywhere in between. In any case, the arms 28 preferably extend through slots 48 in the shroud 20 and have a substantially rectangular cross-section. The rectangular cross-section allows the arms 28 to maximize utilization of the slots 48 in the shroud 20 while minimizing the size of the slots 48 in the shroud 20.

The arms 28 may include outwardly extending protrusions 49 to selectively engage the main body 24, thereby rigidly aligning the axle 26 with the main body 24. More specifically, the arms 28 are preferably inserted through the slots 48 in the shroud 20, pushed together, inserted into the main body 24, and then released. The arms 28 push outwardly on the protrusions 49, which engage the main body's 24 interior, thereby securing the arms 28 to the main body 24. The axle 26 is then seated within the cut-outs 44, thereby rotatably securing the clip 10 to the goggle 14.

The skirt 30 preferably extends forwardly of the main body 24 and maintains close proximity to the shroud 20 during rotation of the clips 10 such that a gap 50 between the shroud 20 and the skirt 30 is preferably maintained at one sixteenth of an inch or less. However, in some cases, the gap 50 may be allowed to expand to approximately one eighth inch, without departing from the present invention. In this manner, the skirt 30 forms an aerodynamic seal with the shroud 20, thereby diverting airflow away from the hinge and preventing snow, wind, dust, dirt, and other contaminants from interfering with the hinge's operation. Furthermore, the skirt 30 and the location of the axle 26 both contribute to conceal the hinge, thereby providing a more aesthetically appealing goggle 14.

While the present invention has been described above, it is understood that other materials and/or dimensions can be substituted. For example, the clip 10 may be made of a different material. However, metal is not preferred as metal is likely to experience or present problems, in cold and snowy environments. With that said, the clip 10 may include metal components, such as an identification badge, that do not experience or present such problems. Furthermore, it should be noted that the goggle 14 is expected to be used with two of the clips 10, one for each side of the shroud 20 and end of the strap 12. These and other minor modifications are within the scope of the present invention.

Having thus described a preferred embodiment of the invention, what is claimed as new and desired to be protected by Letters Patent includes the following:

1. A goggle comprising:
   a lens;
   a shroud surrounding the lens' periphery;
   a strap for holding the shroud adjacent a user's face;
   a clip operable to secure the strap to the shroud, wherein the clip includes an axle offset from a main body by at least one arm which penetrates the shroud, wherein the main body includes a skirt that conforms to the shroud, and wherein the skirt is operable to maintain close proximity to the shroud during pivoting of the clip such that a gap between the shroud and the skirt never exceeds one eighth inch during normal operation of the clip; and
   a concealed hinge for pivotally securing the clip to the shroud.

2. The goggle as set forth in claim 1, wherein the clip has an axis of rotation within the shroud.

3. The goggle as set forth in claim 1, wherein the clip pivots about an axle within the shroud.

4. The goggle as set forth in claim 1, wherein the main body is located outside the shroud and the axle is located inside the shroud.

5. The goggle as set forth in claim 1, wherein the skirt extends forwardly of the main body.

6. A goggle comprising:
   a lens for protecting a user's eyes;
   a shroud surrounding the lens' periphery and extending rearwardly of the lens;
   a strap for holding the shroud adjacent the user's face; and
   a clip operable to secure the strap to the shroud, wherein the clip is rotatably secured to the shroud by a concealed hinge and includes—
      a main body located outside the shroud and secured to the strap, wherein the main body includes a skirt that conforms to the shroud, wherein the skirt is operable to maintain close proximity to the shroud during pivoting of the clip such that a gap between the shroud and the skirt never exceeds one eighth inch during normal operation of the clip, and
      an axle located inside the shroud and offset from the main body.

7. The goggle as set forth in claim 6, wherein the axle is offset from the main body by at least one arm which penetrates the shroud.

8. The goggle as set forth in claim 6, wherein the skirt extends forwardly of the main body.

9. A goggle comprising:
   a rigid lens for protecting a user's eyes;
   a flexible shroud surrounding the lens' periphery, extending rearwardly of the lens, and including vents operable to allow air flow though the goggle in order to prevent fogging of the lens;
   a resilient strap for holding the shroud adjacent the user's face, wherein the strap includes an adjustment buckle to adjust the strap's length such that the goggle may be selectively used with and without a helmet; and
   two clips each operable to pivotally secure the strap to the shroud, wherein each clip includes—
      a main body located outside the shroud and secured to the strap,
      an axle located inside the shroud and offset from the main body by two arcuate arms which penetrate the shroud, and
      a forwardly extending skirt that conforms to the shroud, wherein the skirt is operable to maintain close proximity to the shroud during pivoting of the clips such that a gap between the shroud and the skirt is never exceeds one eighth inch.

* * * * *